US006484062B1

(12) United States Patent
Kim (10) Patent No.: US 6,484,062 B1
(45) Date of Patent: Nov. 19, 2002

(54) COMPUTER SYSTEM FOR STRESS RELAXATION AND OPERATING METHOD OF THE SAME

(76) Inventor: Hyun Kim, 507-401, 5th Pyunghwa Jookong Apt., Pyunghwa-Dong, Wansan-Ku, Junjoo-Shi, Junrabook-Do (KR)

(*) Notice: Subject to any disclaimer, the term of this patent is extended or adjusted under 35 U.S.C. 154(b) by 0 days.

(21) Appl. No.: 09/450,598

(22) Filed: Nov. 30, 1999

(30) Foreign Application Priority Data

| Jan. 28, 1999 | (KR) | 99-0002772 |
| May 11, 1999 | (KR) | 99-0007940 |
| Sep. 9, 1999 | (KR) | 99-038330 |

(51) Int. Cl.[7] .............................................. G06F 17/00
(52) U.S. Cl. .............................. 700/90; 700/1; 600/26; 600/27; 600/28
(58) Field of Search ........................ 700/1, 90; 600/26, 600/27, 28

(56) References Cited

U.S. PATENT DOCUMENTS

| 5,318,503 A | * | 6/1994 | Lord | 600/27 |
| 5,676,633 A | * | 10/1997 | August | 600/27 |
| 5,681,259 A | * | 10/1997 | August | 600/27 |
| 5,947,908 A | * | 9/1999 | Morris | 600/484 |
| 5,949,522 A | * | 9/1999 | Manne | 352/85 |
| 6,007,569 A | * | 12/1999 | Frenkel et al. | 607/88 |
| 6,102,846 A | * | 8/2000 | Patton et al. | 600/26 |
| 6,169,595 B1 | * | 1/2001 | Manne | 352/85 |
| 6,254,527 B1 | * | 7/2001 | August | 600/27 |
| 6,282,458 B1 | * | 8/2001 | Murayama et al. | 700/239 |

* cited by examiner

Primary Examiner—Thomas Black
Assistant Examiner—Ronald D Hartman, Jr.
(74) Attorney, Agent, or Firm—GWIPS (57) ABSTRACT

A new concept of computer system is provided to relax stresses such as fatigue, VDT syndrome, occupational diseases or psychogenic possibly gained from long hours of computer usage. This new computer system is able to divert the negative effects of conventional computer to affirmative effects by introducing the aroma therapy. The new computer system provides not only the data programs of establishing, playing execution and controlling, but also the stress relief program comprising acoustic therapy, color therapy, fragrance therapy and tactual therapy and a stress perception program. The stress relief program is operated by an emission device through a converter. The equipment of the stress relief is installed on a peripheral device of computer such as a speaker, keyboard or monitor. The new concept of computer system for stress relaxation originates a combination of the computer system and the natural therapies applied the human senses like sight, hearing, feeling and smelling senses. With this new computer system, the computer user has a merit of stress relief during the computer operating.

23 Claims, 8 Drawing Sheets

COMPUTER SYSTEM FOR STRESS RELAXATION AND OPERATING METHOD OF THE SAME

BACKGROUND OF THE INVENTION

1. Field of the Invention

The present invention relates to a computer system for stress relaxation and an operating method of the computer system; more particularly, relates to a computer system and operating method providing stress relief means comprising acoustic therapy, color therapy, fragrance therapy or tactual therapy to relax stress, fatigue or psychological disorder possibly gained from the long hour operation of computer.

2. Description of Prior Art

Recently, as increasing the operation of computers, many computer users are commonly suffering the symptoms of stress or VDT syndrome caused from the long hour operation of computer, and this fact turns out a serious social problem. Therefore, a new computer system is required to resolve this sort of problem as well as maximize the working efficiency. To do this, the new computer system adopted a stress relaxation devise is appeared to divert a negative effect of computer operation to an affirmative effect. It is one of the best desirable and efficient methods to apply the human sensibility for a stress relief.

Some conventional computers have equipped with a sensibility function such as an audio-visual effect, some fragrance spraying kits along with IC chips have been used. But, these sorts of fragrance spraying kits are simply purifying or ventilating the air, or removing odors by spraying fragrance. Meanwhile, the conventional computer systems are furnished a screen saver mode, but the screen saver mode is a monotonous function and simply displays a picture on a monitor screen.

Furthermore, the conventional emitting device is controlled only the spraying quantity or spraying time of fragrance according to the pre-fixed emission program within an internal circuit of an IC chip or transistors.

Other conventional computer systems are provided a music function during the screen saver mode, but the playing music is not matched to the displayed picture on the monitor screen. If an olfactory function were combined to the conventional audio-visual function, the stress relief function would be more effectively increased. If the combined sensibility function were connected to the computer system, the effect of stress relief would be more affirmatively increased than one expected with great synergic effect.

With regard to the prior references, the Korean Unexamined Patent Publication No. 98-83351 discloses a picture image and fragrance emitting system in multimedia apparatus, such as television, video player, personal computer or electronic game player. This kind of apparatus provides the fragrance emitting system installed in the multimedia apparatus like a television set, and emits the pre-fixed amount of fragrance simultaneously matched to a suitable visual condition. The conventional technology of the fragrance emitting system combines an audio-visual signal with an olfactory signal by using a VCR signal mixer and encoding a suitable odor information to a pictorial information data during the photographing, manufacturing or editing multimedia. For reproducing the combined signal, an olfactory signal is generated through decoding of olfactory signal separated from a VCR signal by a separator. However, the conventional technology of the fragrance emitting system is inconvenient for daily usage because the operation of the device is complicate and required additional appendent.

SUMMARY OF THE INVENTION

An objective of the present invention is to provide a computer system for stress relaxation and an operating method of the computer system. More specifically, the objective of the present invention is to provide a computer system and operating method which possibly make the computer user relax the stress or VDT syndrome by stimulating the user's nerve organs such as the sense of sight, hearing, feeling or smelling.

Another objective of the present invention is to provide a computer system adopting a naturopathy concept being combined an audio-visual stimulation program applied to a personal computer, a notebook computer, a server and other sorts of computers with a nasal-tactual stimulation program applied to a newly developed converter. One of the peripheral devices of computer system perceives computer user's physical conditions, and the user's physical conditions are recorded and compared with the preset data in the program.

Another objective of the present invention is to provide a computer system outputting a signal generated from the software program which is simply modified to the existing computer system, transmitting the signal to an interface, emitting fragrance matched with a picture on a monitor screen and a playing music, and stimulating the computer user's nerve organs for stress relief. The computer system provides various aroma environments depending on the emitting program which is combined according to the input signals during reproducing and controlling the program.

Another objective of the present invention is to provide a computer system for offering the best pleasant environment to a computer user depending on computer user's physical condition, such as a blood pressure or a quantity of blood circulation.

Another further objective of the present invention is to provide a fragrance emitting system which a computer user can control intensity or spraying time of fragrance.

Another further objective of the present invention is to provide a stress relaxation system being able to upgrade or modify the programs via a computer network such as internet. And the system being able to immediately respond the unexpected changes informed from the outside of the system, such as the worse exterior environment or weather change, so as to upgrade or modify the program on time.

In order to achieve the above objectives, the computer system for stress relaxation, displaying a preset picture on a monitor screen according to a pictorial information data, and emitting a predetermined amount of fragrance through an emitting device according to a emission information data, comprises:

data storage means for storing said pictorial information data and said emission information data;

a microprocessor for searching and outputting a desired pictorial information data and a desired emission information data corresponding to said desired pictorial information data from said data storage means in response to an input signal, and having a capability of searching and retrieving said desired pictorial information data and emission information data from random positions of said data storage means;

a monitor for displaying said picture on the monitor screen according to said pictorial information data retrieved from said microprocessor in response to said input signal;

a converter for converting said emission information data corresponding to said pictorial information data retrieved from said microprocessor to an output signal, and outputting said output signal; and a fragrance emission device for emitting fragrance in response to said output signal from said converter.

It is desirable to generate the input signal when a predetermined time is lapsed and no input information data is issued from inputting devices including a keyboard or a mouse.

It is desirable that the data storage means further stores acoustic information data, the microprocessor simultaneously outputs the pictorial information data, and the emission information data and the acoustic information data corresponding to the pictorial information data from the data storage means in response to the input signal, and wherein a sound is output through a speaker in response to the acoustic information data.

It is desirable that the data storage means further stores tactual information data, wherein the microprocessor simultaneously outputs the pictorial information data, and the emission information data and the tactual information data corresponding to the pictorial information data from the data storage means in response to the input signal, and wherein a tactual stimulation device stimulates the tactual sense of computer user through an output signal generated in response to said tactual information data.

It is desirable that the computer system further comprising:

means for issuing a physical information signal according to perception of a computer user's physical information, a microprocessor for searching a proper pictorial information data and a proper emission information data corresponding to the perceived user's physical information and outputting the proper pictorial information data and emission information data from the data storage means in response to the physical information signal;

a converter for converting the proper emission information data corresponding to the proper pictorial information data retrieved from the microprocessor to an output signal, and outputting the output signal; and a fragrance emission device for emitting fragrance in response to said output signal from said converter.

The means for generating the physical information signal may include a stress perception sensor attached to input devices, such as a keyboard or a mouse, and a sensor converter for converting perceived signal from the stress perception sensor to the physical information signal.

The physical information may be the physical information including user's body temperature, blood pressure, pulse and a quantity of blood circulation.

It is desirable that a frequency, amount, interval or cycle of the information data stored in said data storage means is adjustable and selectable by the user.

It is desirable that the information data stored in the data storage means is modifiable at imminent through a computer network or an internet.

The fragrance emission device is possibly installed interior of a main computer frame, and used a same power source of the computer. Alternately, the fragrance emission device is possibly attachable to the exterior of a main computer frame, and used a different power source of the computer. Especially, the fragrance emission device is possibly attachable to a peripheral device of the computer such as a monitor, keyboard or speaker. Preferably, the fragrance emission device includes a container and an electric on-off spray switch with a solenoid valve.

Another further objective of the present invention is to provide an operating method of a computer system for stress relaxation for displaying a preset picture on a monitor screen according to a pictorial information data and emitting a preset amount of fragrance through an emission device according to an emission information data, the operating method comprising the steps of:

issuing a physical information signal according to perception of a computer user's physical information;

receiving the physical information signal;

searching a proper pictorial information data and a proper emission information data corresponding to the perceived computer user's physical information;

outputting the proper pictorial information data from the data storage means in response to the physical information signal;

displaying a proper picture in response to the proper pictorial information data from the microprocessor;

outputting the emission information data to an interface;

converting the proper emission information data corresponding to the proper pictorial information data retrieved from the microprocessor to an output signal, and outputting the output signal; and operating a fragrance emission device in response to the output signal to emitting a proper fragrance.

It is desirable that the method further includes the steps for searching a desirable information data from the data storage means of optional information data, and outputting the information data selected by the user for the pictorial information data and the emission information data.

The computer system for stress relaxation of the present invention is provided to systematically connect the whole or main part of programs to an interface, emitting device, stress perception device and the home page.

For the computer programs, the system is preferably provided that the computer user is able to install and implement the reproduction programs modified the various data programs furnished by home page. The computer program is also provided to combine a picture file which is suitable data program for implementing the concept of color therapy to a music file. Moreover, the computer program is provided to automatically operate the reproduction program according to a signal being sent from a peripheral device such as a mouse or a keyboard capable to perceive user's stress.

The computer program is also provided that a program signal is transformed to an electric signal when the data program is operated in a reproduction program, and at the same time the interface section operates the emitting device. Especially, it is provided that the program can be automatically operated when the program receives the signal sent from the peripheral device such as a mouse or a keyboard capable to perceive the user's stress.

The computer program is also provided that an emitting device is able to emit fragrance according to the program transmitted from interface section. Consequently, the picture based on the concept of color therapy displayed on monitor screen, the suitable music based on the concept of acoustic therapy corresponding to the displayed picture on monitor screen, and the fragrance based on concept of fragrance therapy which is in harmony with the displayed picture and playing music.

As described above, the present invention system is provided an effective system for relaxing the stress, fatigue or VDT syndrome possibly gained during the computer works. It should be realized that the synergic effect of each program is obtainable based on concept of the music, color, aroma and tactual therapy. These effects are obtained from the audio-visual stimulation modified the existing computer system, and nasal-tactual stimulation combined with the emitting device and the tactual recognition device. Because this system can relax the stress depending on the computer user's condition by automatically detecting the user's stress, this present invention offers the extensive usage of computer.

All of objectives and advantages of this present invention will become apparent from the following detailed description of the preferred embodiments with the drawings.

DETAILED DESCRIPTION OF THE INVENTION

A detailed description of the preferred embodiment of the present invention is described in conjunction with the drawings.

Figure 1:
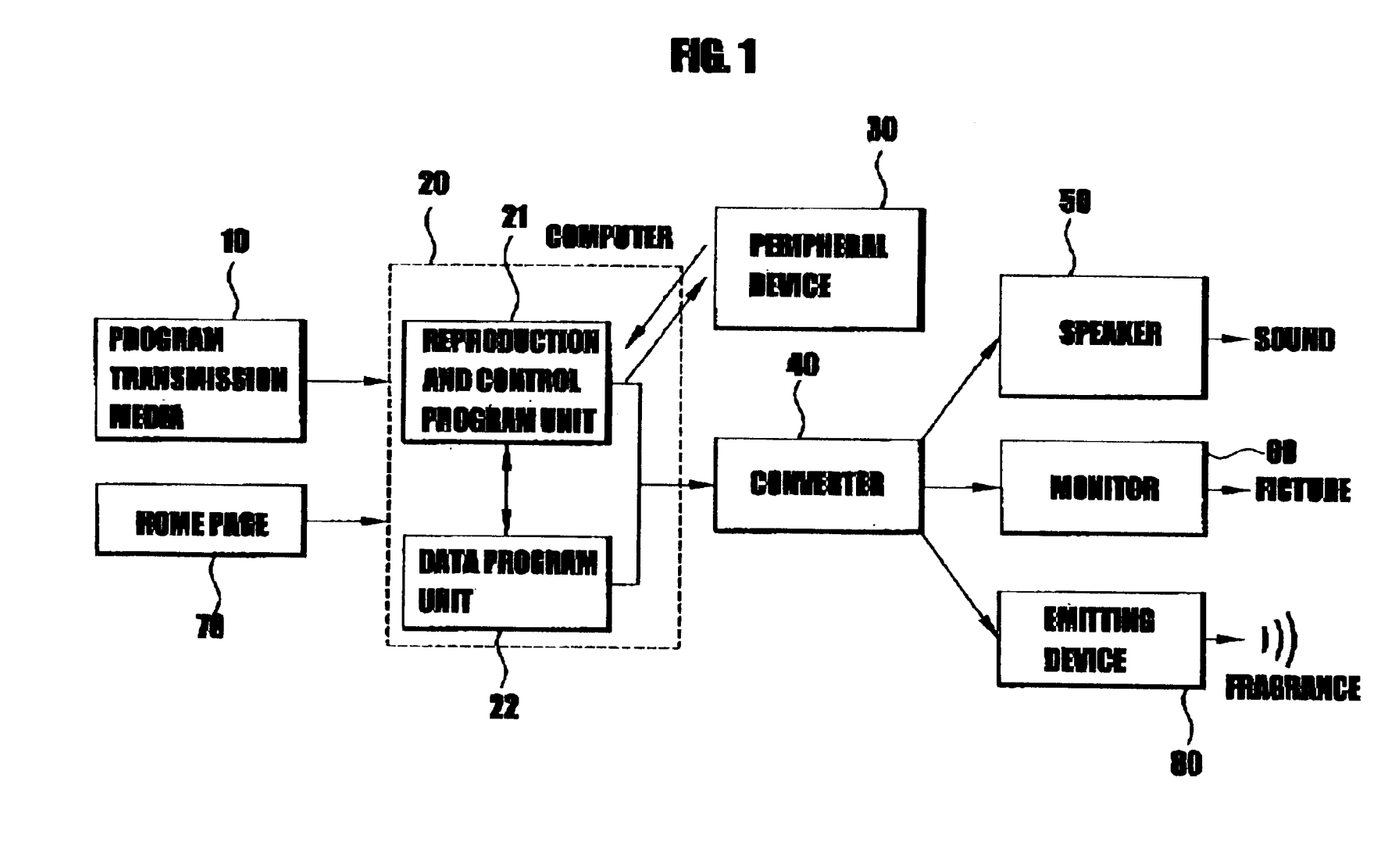
FIG. 1 is a schematic diagram showing the computer system for stress relaxation of the present invention.

FIG. 1 is a schematic diagram showing a computer system for stress relaxation of the present invention. The present invention is initiated with a naturopathy program which is programmed by downloading the data programs furnished from a home page 70 through an internet program, and installed a reproduction program and a control program in an operator's computer system through a remote control apparatus or a program transmission media 10. The reproduction program and the control program are stored in a reproduction and control program unit 21, and the data programs are stored in a data program unit 22. When an input signal issues from a peripheral device 30, such as a mouse or a keyboard, a microprocessor activates, and an output signal from the microprocessor is converted to a proper control data and signal through a converter 40. Then, a music based on a concept of music therapy is played through a speaker 50, a picture based on a concept of color therapy is displayed on a monitor screen 60, fragrance based on a concept of fragrant therapy is sprayed by an emitting device 80. A program transmitting media includes the various recording devices, such as a CD, a floppy disc and a cassette tape recorder, and a remote control device includes the various wireless transmitting-receiving instruments, such as a remote controller, a cellular phone and a beeper.

The present computer system is provided the high efficiency in working by actively operating the stress relief program with perceiving a computer user's physical condition through a perception sensor attached on a peripheral device of computer, such as a keyboard or a mouse.

The programs based on the naturopathy comprise a reproduction and control program, a stress perception program and the data programs. The data programs for various therapies comprise a color therapy, a fragrant (or aroma) therapy, a tactual therapy and an acoustic therapy program. When these programs are installed in a computer system, the programs are compiled the various forms, like a base picture and a screen saver being linked to a converter to match with each program. And the data programs enable to change any time through home page as a form of portal site. For the program based on the concept of acoustic therapy, all kinds of sound are included, music, artificial sound, natural sound, the sound of affirmative effects that gives human refreshes, fatigue relief, and disorder curable sound. For the program based on the concept of color therapy, all colors are included, the color of affirmative effects such as fatigue relief, stress relaxation and disorder relief including natural or artificial color, figure, print, picture and photo. Also, in the program based on the concept of aroma or fragrant therapy, all kinds of fragrance are included, natural odor and artificial odor.

The transmission media for recording the naturopathy program has means of recording media such as internet home page, CD, diskette and a remote controller, and installation capability in the computer systems.

Figure 2:
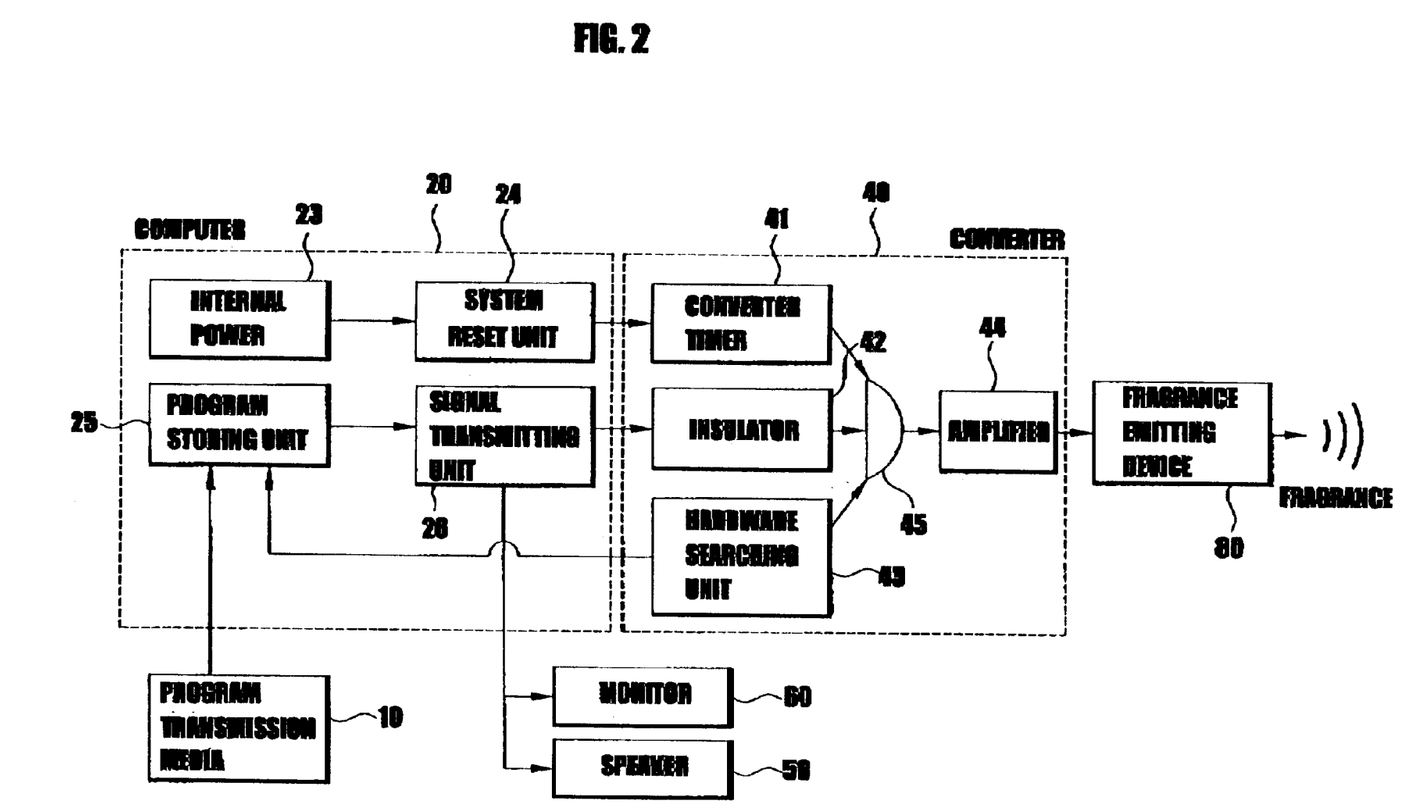
FIG. 2 is a detailed diagram showing the computer system for stress relaxation of the present invention with an internal model emission device.

The emitting device of the present invention enables to install either internal or external of the users' computer. FIG. 2 shows a detail drawing of an internally installed model and using same power of the computer. The signal from the program-installed computer 20 is transmitted to the converter via two channels of circuits. The fragrance emitting initiates after a internal power 23 is on and a computer system reset unit 24 is activated, when a converter timer 41 receives a signal and controls to transmit the signal to an emitting device 80 during a proper time. If the timer completes the controlling, the controlled program of a program storing unit 25 is transmitted to an insulator 42 of a converter through a signal transmitting unit 26. Simultaneously, a hardware searching unit 43 activates for searching the programs. A series of the procedures is combined and analyzed through a signal comparing and processing unit 45. The completed signals is amplified through an amplifier 44, and is transmitted to activate the fragrance emitting device 80 for spraying the fragrance.

A picture displaying is same as a conventional computer system, and is executed on a monitor screen for reproducing the data program through the transmitting unit 26 and a graphic card. At this time, the screen picture being composed with the several pictures and photos is displayed in the various ways for properly matching with the music and fragrance. The sound execution is same as a conventional method and is activated by a speaker 50 through transmitting unit and the sound card after the data programs are reproduced. At this time, the composition of sound is controlled for the sorts, component, loudness and length for harmony with the display picture.

Also, the converter includes a converting capability for stimulating the nerves of smell and touch, beside the existing sound card and video card.

A converter for emitting fragrance to stimulate the olfactory sense and the tactual sense is installed either internal of the peripheral device of the computer system, such as the speaker, monitor, keyboard, remote controller and mouse or external of the computer system separated from the computer. A power source for the converter is utilized either an internal power source of the computer system or an external power source. The fragrant emitting device comprises an electronic spraying kit and the container of the fragrance. The operation of the fragrant emitting device is controlled by the control program. An electronic on-off spray switch of the fragrant emitting device being furnished an electronic valve or a motor enables to operate one or more of fragrance containers. The power source of the fragrant emitting device is utilized either an internal power source of the computer system or an external power source.

Figure 3:
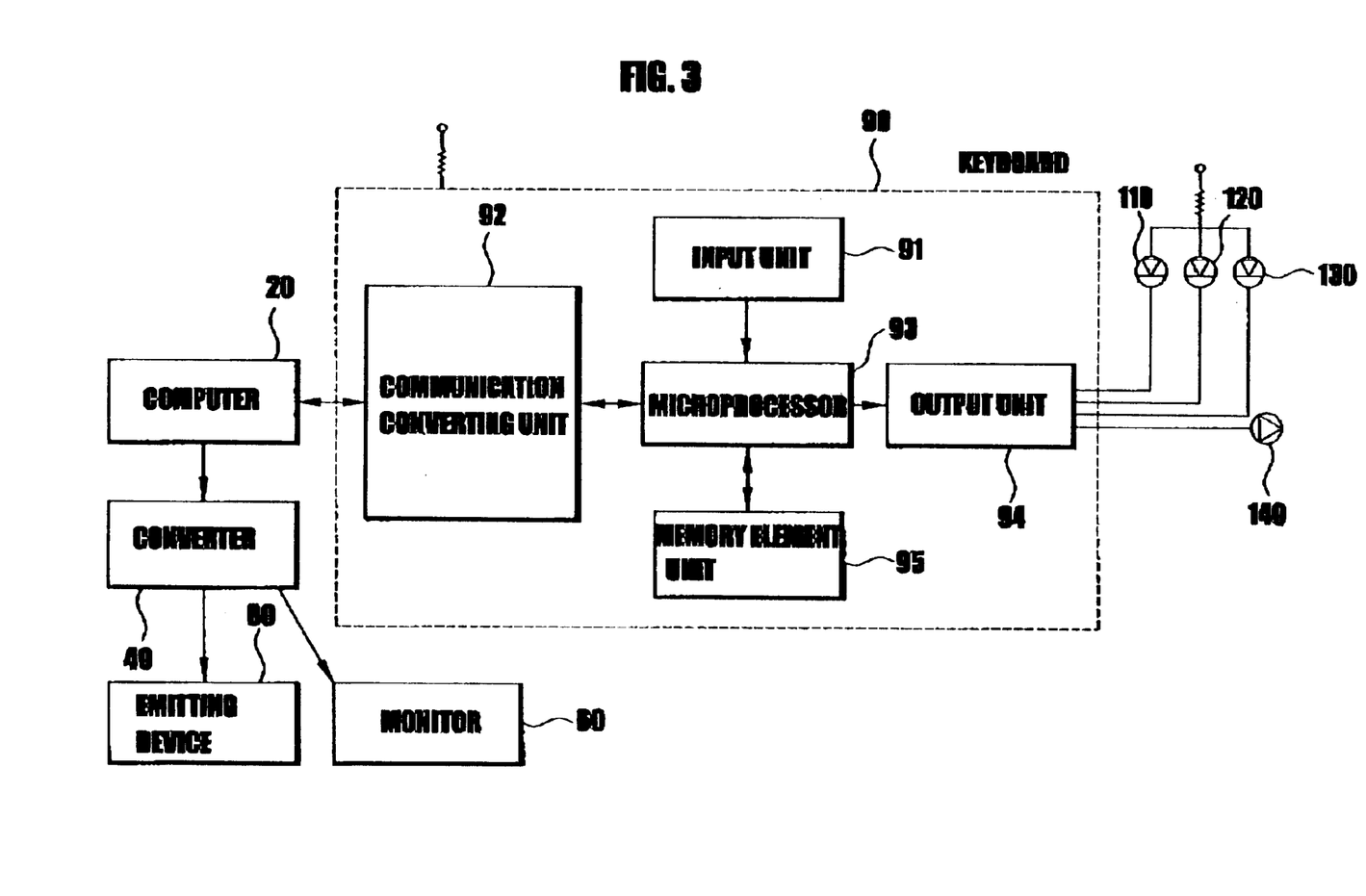
FIG. 3 is a detailed diagram showing the computer system for stress relaxation of the present invention with an internal model emission device using keyboard.

FIG. 3 is a practical example of a converter installed inside of a keyboard of computer system. A signal transmitted to the converter 40 installed inside of the keyboard 90 from the main computer 20 and a signal issued from an input unit 91 are combined to issue an output signal through the output unit 94 controlled by the microprocessor 93 and the memory element unit 95 installed inside of the keyboard. In case of developing the existing keyboard, the output unit 94 uses three buttons of "Num Look" 110, "Caps Look" 120 and "Scroll Look" 130 for outputting the output signals. But a button of an "Emitting SIG" 140 is added in the present invention for spraying fragrance through the fragrant emitting device. At the same time, the proper music and picture are executed through the speaker 50 and monitor screen 60, respectively. The reference numeral 92 is a communication converting unit.

Figure 4:
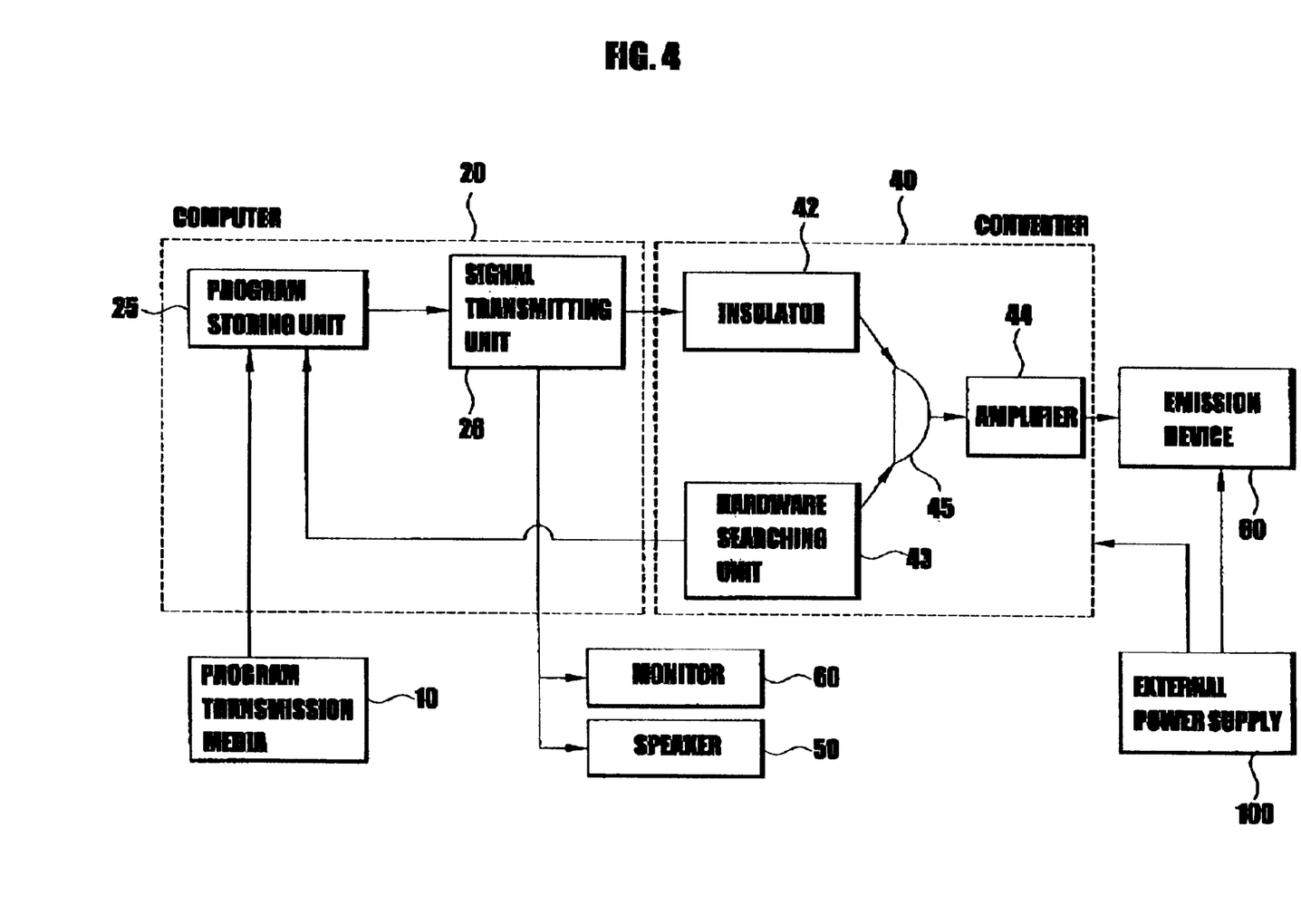
FIG. 4 is a detailed diagram showing the computer system for stress relaxation of the present invention with an external model emission device.

FIG. 4 is a detailed drawing of a converter installed external of the computer system. A program from the program storing unit 25 installed in the computer 20 transmits signals to the insulator 42 of the converter 40 through the signal transmitting unit 26. After the hardware searching unit 43 of the converter is operated, the signals are combined and analyzed by the signal comparing and processing unit 45 and amplified by the amplifier 44. Consequently, a fragrance is sprayed when the signal is transmitted to the fragrance emitting device 80. The fragrance emitting device 80 for external model is connected to a port of the computer, and executed the screen picture and music same method as the internal model. An external power source 100 is connected to the converter 40 and the fragrance emitting device 80 from the outside of computer 20 unlikely of the internal model.

The fragrance emitting device 80 of the internal and external models comprises the electronic on-off spray switch and the fragrance container. The electronic on-off spray switch of the electronic emitting device includes the electronic valve furnished the solenoid valve or other type of valve and a motor. The operation of the electronic valve is controlled by the converter and varied depending on the controlling programs. The connecting means for the electronic emitting device and the fragrance container includes a coupling means or a thread means of direct or indirect connection. The interval and amount of fragrance spraying is controlled by the emitting control program, and activated through the converter of the fragrance emitting device. The converter and the fragrance emitting device are installed either one of peripheral device, such as the keyboard, mouse, monitor, remote controller and speaker.

Figure 5:
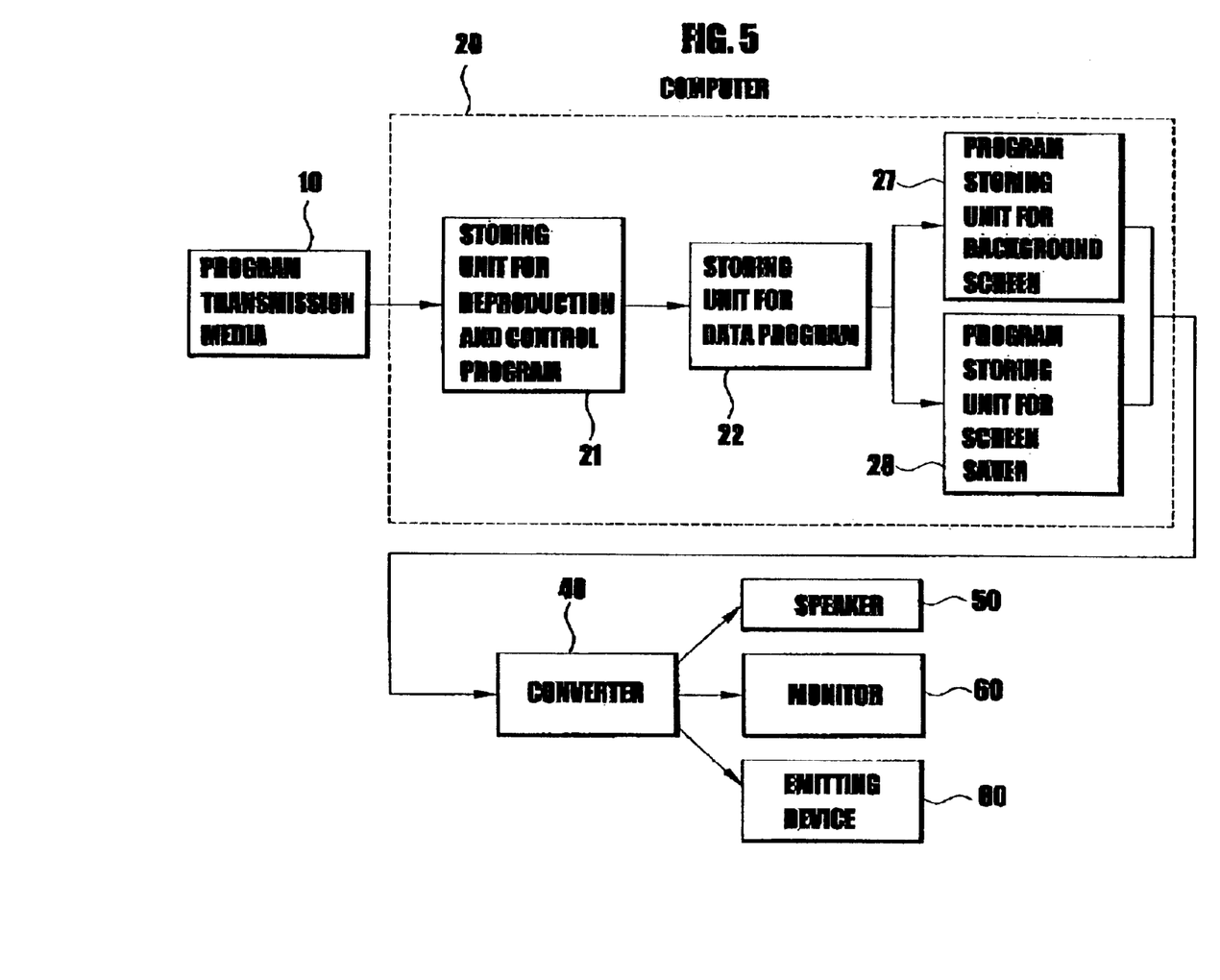
FIG. 5 is a detailed diagram showing the computer system for stress relaxation of the present invention adapted to the screen saver and base picture.

FIG. 5 is another practical example applied to the base picture and screen saver. This system provides that the base picture is automatically appeared on the monitor screen, the music is sounded through the speaker and the fragrance is sprayed through the emitting device whenever the operator turns on the computer system. The system provides a capability of varying the mode whenever the user begins a new operation. This system also provides the effect of stress relaxation by operating a data program which is programmed based on the concept of color, acoustic and aroma therapy with modifying of the conventional screen saver to relax the fatigue, occupational and psychogenical stress gained during a computer operation. The operation of the stress relaxation programs would be initiated when the naturopathy programs are installed in the computer system from the program transmitting media 10. When the programs are installed in the program storing unit for reproduction control program (21) and data program (22), the programs which are automatically displayed the base picture and screen saver on the monitor screen enables to operate depending on the inputted program corresponding to the selected and controlled input data.

When the program is activated, the base picture (27) and screen saver (28) based on each therapy program are executed to display on the monitor screen, play music via the speaker, and emitting fragrance via electronic emitting device 80 being controlled by the converter 40. For example, if the computer user selects a pine tree forest picture or photo among the stored color therapy files, sounds of breeze, stream and bird song among acoustic therapy files, which are related to the pine tree forest picture, and pine tree fragrant among aroma therapy files, the selected programs are combined to stimulate the user's nerves of sight, hearing and smelling for the stress relief. At this time, the data programs related the three kinds of the therapy programs could be combined to provide one program file.

Figure 6:
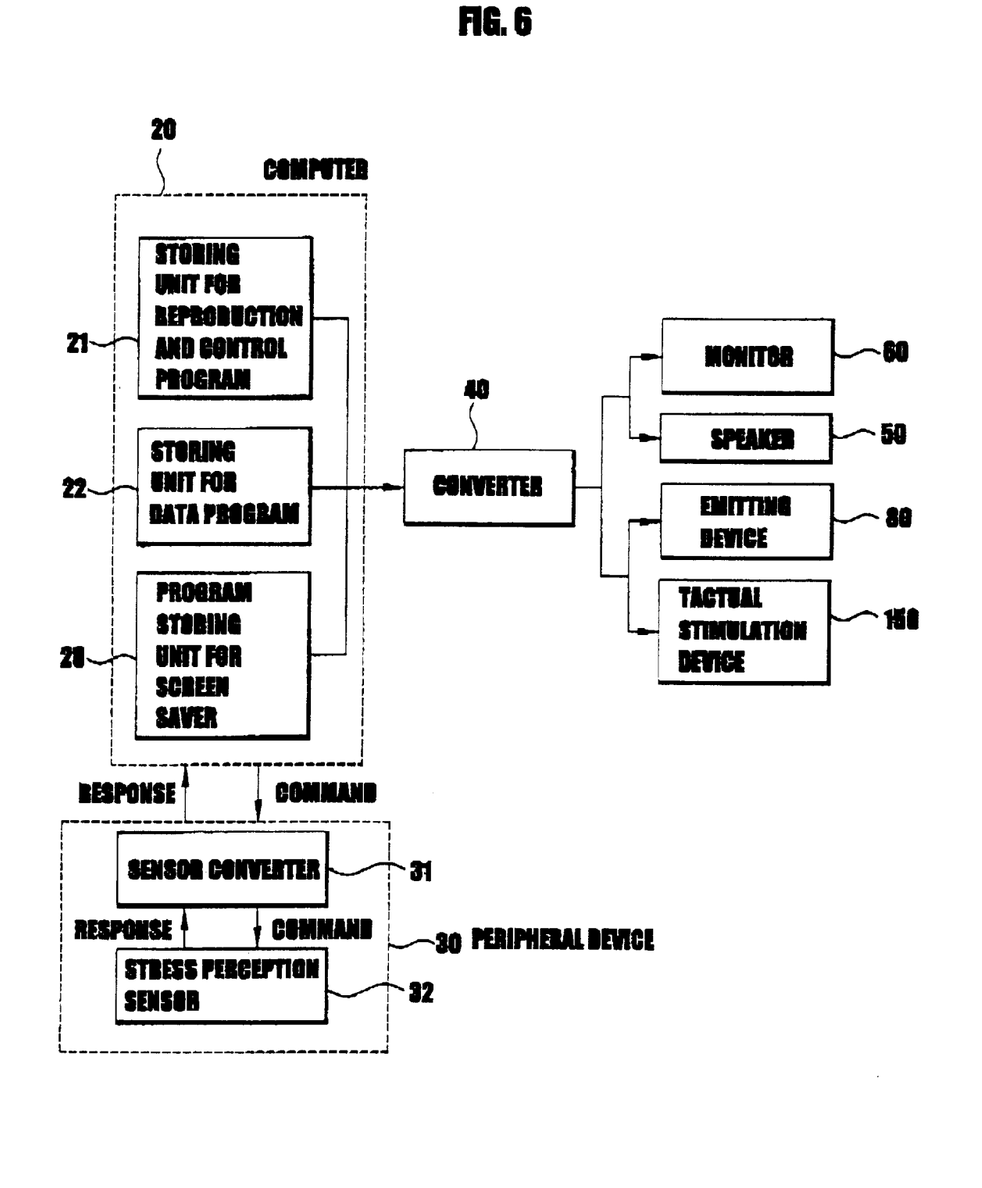
FIG. 6 is a detailed diagram showing the computer system for stress relaxation of the present invention using an automatic perception apparatus.

FIG. 6 shows the computer system having a stress perception sensor. A stress perception or detection sensor 32 attached on the peripheral device 30 such as a keyboard or a mouse perceives the computer user's stress status. The stress relief program will be operated through the sensor converter 31 of the computer or microprocessor depending on the perceived user's stress status to achieve the high working efficiency. For instance, the computer user's stress status could be estimated depending on the user's temperature, amount of blood circulation and pulse perceived by the perception sensor 32 and by observing the user's complexion through a video camera. The tactual stimulating device includes an electronic stimulator and electric vibrator or other type of stimulator to stimulate the user's tactual nerves in many ways.

Figure 7:
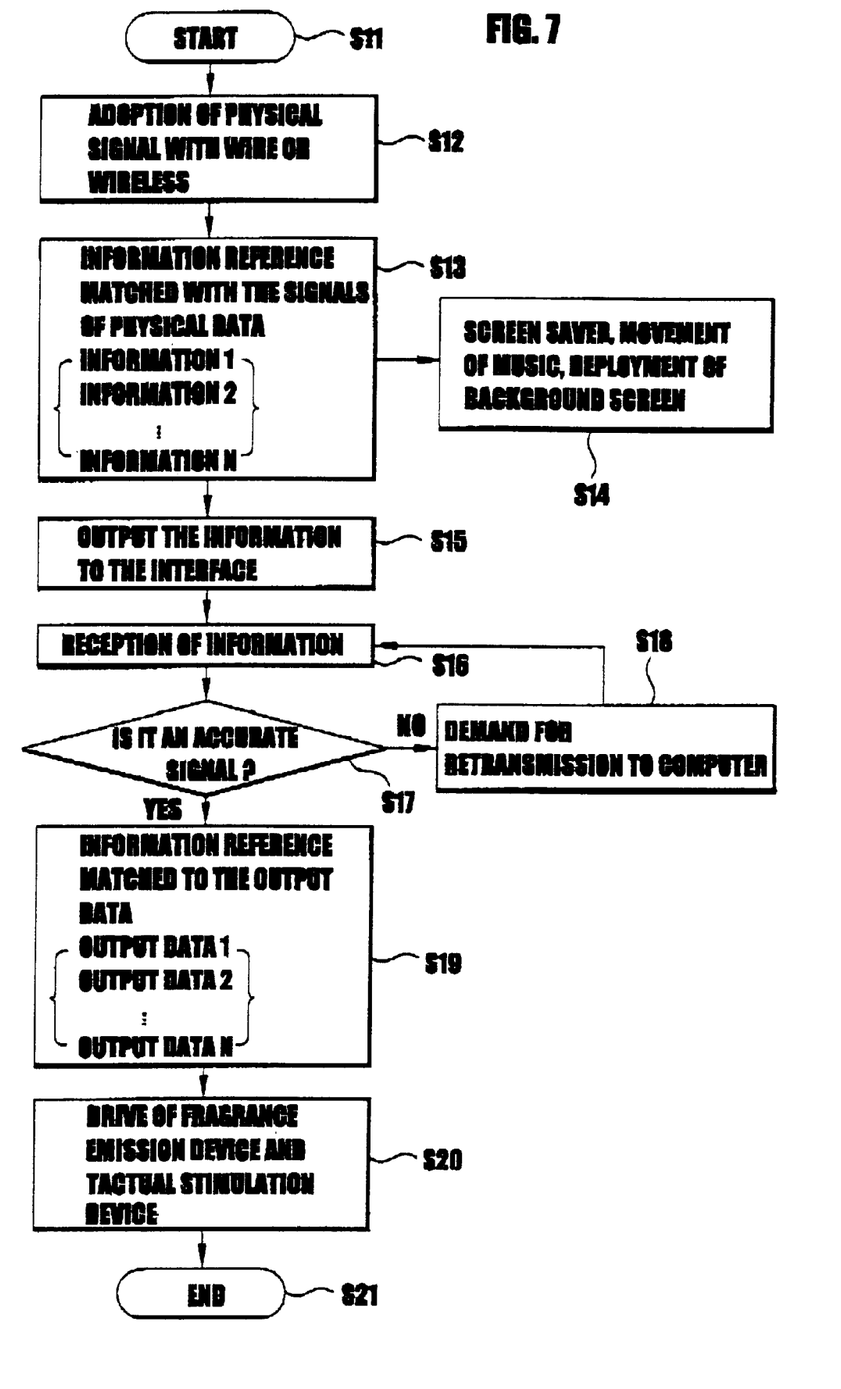
FIG. 7 is a flow chart explaining the operation of the computer system for stress relaxation of the present invention.

With regard to FIGS. 1 and 7, the operation of computer system for stress relaxation will be described as follows.

When the operation of the computer system is started (S11), the computer or microprocessor 20 receives input signals from the peripheral device 30 such as a keyboard or a mouse through wire or wireless (S12). These signals might be more than one of user's physical conditions such as temperature, pulse and amount of blood circulation perceived by the peripheral device of the computer, the user's complexion observed by a video camera or a signal of screen saver mode responding to no input data signals after a certain time lapsed. In a data searching step (S13), the microprocessor searches a proper data stored in the computer 20 corresponding to the received user's physical information. In the screen saver mode step (S14), the base picture and music file execute simultaneously to display the base picture on the monitor screen, and play music through the speaker at the screen saver mode. In a step outputting the information data to the interface (S15), the fragrant emitting information data retrieved in the step S13 are transmitted to the converter as an interface. The fragrant emitting information data received by interface in the step S16 is checked whether the data communicates correctly (S17). If an error is found, the signal commands to return to the previous step S16 in order to correct the error. If there were no error found, an output data step (S19) would start to search the output data matched to the fragrant emitting information data. The output data are related to the sort of spraying device, fragrant intensity and spraying time. Subsequently, the fragrance emitting device (80) and the tactual stimulation device (not illustrated) corresponding to the data signals will be executed (S20). The interface notifies the computer of the fact that the signals for executing the programs successfully input through the interrupt (S21).

Figure 8:
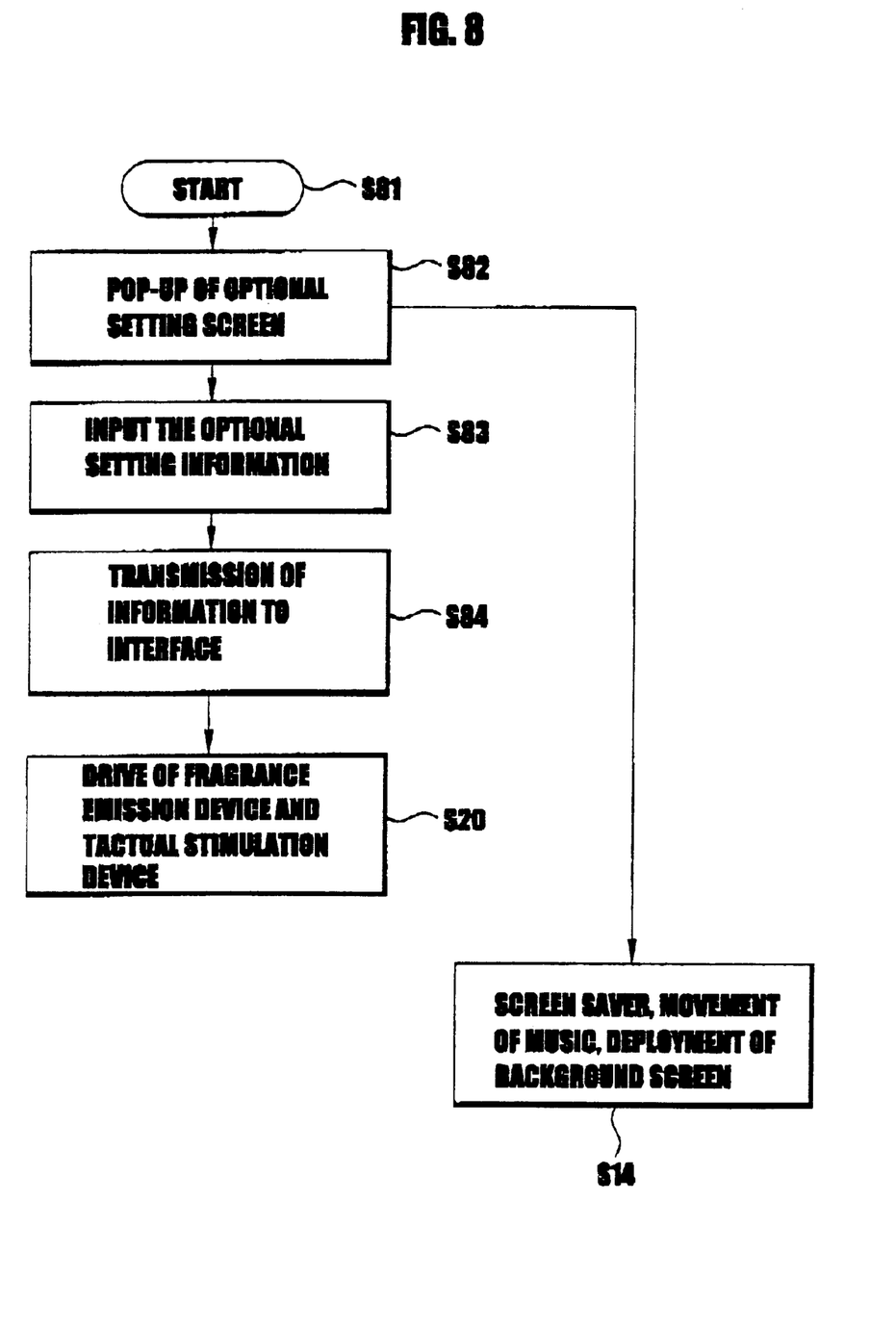
FIG. 8 illustrates a subroutine of the step in another preferred embodiment of the present invention according to the step of searching information data corresponding to physical information data in FIG. 7.

On the other hand, if the fragrant emitting data were searched to be matched with the signals of user's physical information in the step S13, the fragrant emitting data could be selectively adjusted by the computer user. FIG. 8 shows a subroutine for searching data corresponding to the user's physical information. The program starts at step S81. The monitor screen of the computer system displays an optional screen picture (S82), and inputs the optional emitting information data (S83). Simultaneously, the speaker outputs music and the monitor screen displays picture (S14). At the same time, the input data at step S83 inputs the above data of emitting information to transmit the data to the interface (S84). Finally, the fragrance emitting device and tactual stimulating device are executed (S20).

The present invention could be applied to the fields of industries, such as agriculture, fishery, stock farming and interior decoration industry.

As will be appreciated from the foregoing description, it will be apparent to those skilled in the art that various changes and modifications can be made without departing from the spirit of the present invention. Thus, the scope of the invention is not limited to the foregoing description of the present embodiments.

What is claimed is:

1. A computer system for stress relaxation enabled to display a preset picture on a monitor screen according to a pictorial information data, and emits a predetermined fragrance through an emission device according to an emission information data, comprising:
   data storage means for storing said pictorial information data and said emission information data;
   a microprocessor for searching a desired pictorial information data and a desired emission information data corresponding to said desired pictorial information data from said data storage means in response to an input signal, and outputting a selected pictorial and emission information data, and having a capability of searching said desired and retrieving said selected pictorial information data and emission information data from random positions of said data storage means;
   a monitor for displaying said preset picture on the monitor screen according to said pictorial information data retrieved from said microprocessor in response to said input signal;
   a converter for converting said emission information data corresponding to said pictorial information data retrieved from said microprocessor to an output signal, and outputting said output signal; and
   a fragrance emission device for emitting said predetermined fragrance in response to said output signal from said converter.

2. The computer system for stress relaxation as set forth in claim 1, said input signal being generated, where no input information data is issued from input devices including a keyboard or a mouse during a predetermined time.

3. The computer system for stress relaxation as set forth in claim 1,
   wherein said data storage means further stores acoustic information data,
   wherein said microprocessor simultaneously outputs said pictorial information data, and said emission information data and said acoustic information data corresponding to said pictorial information data from said data storage means in response to said input signal, and
   wherein a sound is output through a speaker in response to said acoustic information data.

4. The computer system for stress relaxation as set forth in claim 1,
   wherein said data storage means further stores tactual information data,
   wherein said microprocessor simultaneously outputs said pictorial information data, and said emission information data and said tactual information data corresponding to said pictorial information data from said data storage means in response to said input signal, and
   wherein a tactual stimulation device stimulates a tactual sense of a computer user through another output signal generated in response to said tactual information data.

5. The computer system for stress relaxation as set forth in claim 1, wherein a kind, amount, interval or cycle of said emission fragrance is adjustable and selectable by a user with altering said emission information data stored in said data storage means.

6. The computer system for stress relaxation as set forth in claim 1, wherein said information data stored in said data storage means is modifiable through a computer network or an internet.

7. The computer system for stress relaxation as set forth in claim 1, said fragrance emission device being installed interior of a main computer frame, and using a power source for said main computer.

8. The computer system for stress relaxation as set forth in claim 1, said fragrance emission device being attachable to exterior of a main computer frame, and using a different power source from that of said main computer or using a power source for said main computer.

9. The computer system for stress relaxation as set forth in claim 1, said fragrance emission device being attachable to a peripheral device of a main computer including a monitor, keyboard or speaker.

10. The computer system for stress relaxation as set forth in claim 1, said fragrance emission device comprising a container and an electric on-off spray switch with a solenoid valve.

11. The computer system for stress relaxation enabled to display a picture on a monitor screen according to a pictorial information data, and emits a fragrance through an emission device according to a predetermined emission information data, comprising:
   data storage means for storing said pictorial information data and said emission information data;
   means for issuing a physical information signal according to perception of a computer user's physical information;

a microprocessor for searching a proper pictorial information data and a proper emission information data corresponding to said perceived user's physical information and outputting said selected pictorial information data and said emission information data from said data storage means in response to said physical information signal;

a monitor for displaying a proper picture in response to said proper pictorial information data from said microprocessor;

a converter for converting said proper emission information data corresponding to said proper pictorial information data retrieved from said microprocessor to an output signal, and outputting said output signal; and a fragrance emission device for emitting fragrance in response to said output data from said converter.

12. The computer system for stress relaxation as set forth in claim 11, said means for issuing said physical information signal including:

a stress perception sensor for perceiving a computer user's physical information, which is attached to an input device of a keyboard or a mouse; and a sensor converter for converting said physical information perceived by said stress perception sensor to said physical information signal.

13. The computer system for stress relaxation as set forth in claim 11, said physical information including user's body temperature, blood pressure, pulse or a quantity of blood circulation.

14. The computer system for stress relaxation as set forth in claim 11, wherein said data storage means further stores acoustic information data, wherein said microprocessor simultaneously retrieves said pictorial information data, said emission information data and said acoustic information data corresponding to said physical information from said data storage means in response to said physical information signal, and wherein a sound is outputting through a speaker in response to said acoustic information data.

15. The computer system for stress relaxation as set forth in claim 11, wherein said data storage means further stores tactual information data, wherein said microprocessor simultaneously retrieves said pictorial information data, said emission information data and said tactual information data corresponding to said physical information from said data storage means in response to said physical information signal, and wherein a tactual stimulation device stimulates the computer user's tactual sense according to another output signal generated in response to said tactual information data.

16. The computer system for stress relaxation as set forth in claim 11, wherein a kind, amount, interval or cycle of said emission fragrance is adjustable and selectable by the user with altering said emission information data stored in said data storage means.

17. The computer system for stress relaxation as set forth in claim 11, wherein said information data stored in said data storage means is modifiable through a computer network or an internet.

18. The computer system for stress relaxation as set forth in claim 11, said fragrance emission device being installed interior of a main computer frame, and using a power source of said main computer.

19. The computer system for stress relaxation as set forth in claim 11, said fragrance emission device being attachable to exterior of a main computer frame, and using a different power source from that of said main computer or using a power source for said main computer.

20. The computer system for stress relaxation as set forth in claim 11, said fragrance emission device being attachable to a peripheral device of a main computer including a monitor, keyboard or speaker.

21. The computer system for stress relaxation as set forth in claim 11, said fragrance emission device comprising a container and an electric on-off spray switch with a solenoid valve.

22. An operating method of a computer system for stress relaxation enabled to display a picture on a monitor screen according to a pictorial information data and emits a fragrance through an emission device according to an emission information data retrieved, the operating method comprising the steps of:

issuing a physical information signal according to perception of a computer user's physical information;

receiving said physical information signal for transmitting to a microprocessor;

searching a proper pictorial information data and a proper emission information data corresponding to said physical information signal, and outputting a selected pictorial information data from said data storage means in response to said physical information signal;

displaying a proper picture in response to said selected pictorial information data being retrieved from said microprocessor;

outputting said selected emission information data to an interface;

converting said proper emission information data corresponding to said proper pictorial information data retrieved from said microprocessor to an output signal, and outputting said output signal; and operating a fragrance emission device in response to said output signal to emitting a proper fragrance.

23. The operating method as set forth in claim 22, wherein said information data stored in said data storage means is modifiable through a computer network or an internet.

* * * * *